United States Patent
Fleissman et al.

(10) Patent No.: US 9,192,550 B2
(45) Date of Patent: Nov. 24, 2015

(54) MAGNETICALLY-ORIENTED COSMETIC FIBERS

(75) Inventors: Leona Giat Fleissman, Ridgewood, NJ (US); Tao Zheng, Nanuet, NY (US)

(73) Assignee: Avon Products, Inc., New York, NY (US)

( * ) Notice: Subject to any disclaimer, the term of this patent is extended or adjusted under 35 U.S.C. 154(b) by 600 days.

(21) Appl. No.: 12/820,696

(22) Filed: Jun. 22, 2010

(65) Prior Publication Data

US 2011/0311597 A1    Dec. 22, 2011

(51) Int. Cl.

| | |
|---|---|
| *A61Q 90/00* | (2009.01) |
| *A61K 8/02* | (2006.01) |
| *A61K 8/27* | (2006.01) |
| *A61Q 5/00* | (2006.01) |
| *A61K 8/73* | (2006.01) |
| *A61Q 19/00* | (2006.01) |
| *A61K 8/81* | (2006.01) |
| *A61K 8/88* | (2006.01) |

(52) U.S. Cl.
CPC . *A61K 8/27* (2013.01); *A61K 8/027* (2013.01); *A61K 8/731* (2013.01); *A61K 8/8129* (2013.01); *A61K 8/88* (2013.01); *A61Q 5/00* (2013.01); *A61Q 19/00* (2013.01); *A61K 2800/61* (2013.01)

(58) Field of Classification Search
CPC ..... A61K 8/027; A61K 8/731; A61K 8/8129; A61K 8/88; A61K 8/27; A61Q 5/00; A61Q 19/00
See application file for complete search history.

(56) References Cited

U.S. PATENT DOCUMENTS

| | | | | |
|---|---|---|---|---|
| 3,767,505 | A | * | 10/1973 | Coran et al. ............ 156/276 |
| 4,585,797 | A | * | 4/1986 | Cioca ..................... 514/773 |
| 5,658,586 | A | * | 8/1997 | Rajaiah et al. .......... 424/435 |
| 5,916,541 | A | | 6/1999 | Stewart |
| 6,599,493 | B2 | | 7/2003 | Collins et al. |
| 7,351,406 | B2 | | 4/2008 | Vidal |
| 2002/0022042 | A1 | | 2/2002 | Castro et al. |
| 2004/0237987 | A1 | * | 12/2004 | Gold .................... 132/201 |
| 2005/0186151 | A1 | | 8/2005 | Giroud |
| 2006/0051382 | A1 | | 3/2006 | Vidal |
| 2007/0009454 | A1 | | 1/2007 | Thevenet |
| 2007/0125396 | A1 | | 6/2007 | Ramet |
| 2008/0127990 | A1 | | 6/2008 | Thevenet |
| 2008/0145428 | A1 | | 6/2008 | Zheng |
| 2010/0112019 | A1 | | 5/2010 | Thevenet |

FOREIGN PATENT DOCUMENTS

| | | |
|---|---|---|
| CN | 2558235 Y | 7/2003 |
| EP | 1644563 A1 | 1/2005 |
| JP | H06145610 A | 5/1994 |
| JP | 3109438 U | 5/2005 |
| WO | 0203832 A1 | 1/2002 |
| WO | WO0203832 A1 * | 1/2002 |
| WO | 2007/067494 A1 | 6/2007 |

OTHER PUBLICATIONS

Realistic Eyebrows from Headcovers.com, retrieved online (Oct. 22, 2013), available online (Jun. 3, 2009) from URL< http://web.archive.org/web/20090603092901/http://www.headcovers.com/11186/real-istic-eyebrows-12/ >.*

Fibers; Technical Literature ref FIB-001; Kobo Products, Inc.; Nov. 10, 2009.

* cited by examiner

*Primary Examiner* — Sue Liu
*Assistant Examiner* — Daniel L Branson
(74) *Attorney, Agent, or Firm* — David M. Joyal; Joan M. McGillycuddy

(57) ABSTRACT

There is provided a dissolvable film polymer matrix that includes a plurality of magnetically responsive kertin-like fibers for application to an individual's face or head. The dissolvable film polymer matrix product includes hairs that are magnetically oriented in a non-random plain to be applied on an individuals face or head to simulate the appearance of the individual's natural hair. Methods of manufacturing and applying the dissolvable polymer matrix product are also disclosed.

16 Claims, No Drawings

MAGNETICALLY-ORIENTED COSMETIC FIBERS

FIELD OF INVENTION

The present invention relates to compositions and methods for improving the appearance of keratin fibers, and in particular eyebrows, through the use of magnetically-oriented cosmetic fibers.

BACKGROUND OF THE INVENTION

The eyebrow is an area of thick, delicate hairs above the eye that typically follows the shape of the lower margin of the brow ridges. The main function of eyebrows is to protect the eye, but they are also important to human communication and facial expression. Furthermore, it is not uncommon for people to modify their eyebrows by means of hair addition or removal, and/or to enhance the appearance of their eyebrows with make up.

As people age, often their eyebrows become thinner or fall out. In addition, people who tweeze their eyebrows sometimes lose the ability to regrow the brows to the full extent of their original form or shape. Often, regrown eyebrows may be uneven or sparse.

Furthermore, as people age, they often experience the loss of small patches of hair on their heads and/or faces. Men with beards also often experience the loss of small patches of hair that might appear unsightly or unattractive.

Oftentimes a person experiencing loss of eyebrows or hair in their beards will use a make-up brow pencil or brow powder to fill in uneven areas or the areas lacking hair so as to create a more uniform appearance with the surrounding hairs. The less hair an individual has on the brow line the more unnatural the look will be using the pencils or powders.

There is a need in the art for compositions and methods for applying keratin-like fibers to an individual's eyebrows or face to create a more natural appearance than brow pencils or powder.

It is an object of the invention to provide keratin-like fibers that are oriented in a non-random manner such that the fibers preferably blend with existing hair and simulate the appearance of the existing hair when applied to an existing area of hair, etc. including areas lacking hair.

SUMMARY OF THE INVENTION

To remedy the deficiencies and disadvantages in the prior art, the present invention thus provides, in one aspect, a product for creating or enhancing the appearance of keratin fibers on an individual's face or head, as well as methods for making the product and methods for applying the product to an individual's face or head.

In one aspect of the invention, there is described a product for creating or enhancing the appearance of keratin fibers comprising: (a) a matrix composed of one or more water-dissolvable polymers; and (b) a plurality of magnetic responsive fibers oriented in a non-random direction and embedded in said matrix.

It is another aspect of the invention to provide a method for preparing a product for creating or enhancing the appearance of keratin fibers comprising: (a) applying an external magnetic field to an aqueous mixture of one or more water-dissolvable polymers and plurality of magnetic responsive fibers so as to orient the fibers in a non-random manner; and (b) removing the aqueous solvent to form a solid or semi-solid film.

It is a further aspect of the invention to provide a method for applying a keratin fiber enhancing film comprising: (a) wetting the surface of an area on an individual's face or head to which the film will be applied; (b) positioning the film on the wetted surface; and (c) allowing the film to dissolve; wherein said film includes a plurality of non-randomly oriented fibers that are adhered to said individual's face or head by a water-dissolvable polymer.

The application of the keratin-like fibers to an individual's face, such as to his or her eyebrows simulates natural brows with hair-like texture. The application of the magnetic force to the magnetic responsive fibers orients the fibers in a non-random manner when applied to an individual's eyebrows, face or head.

These and other aspects of the invention will be better understood by reference to the following detailed description of the invention.

DETAILED DESCRIPTION

In its broadest sense, the present invention contemplates a dissolvable polymer film matrix comprising cosmetic fibers, such as nylon fibers, such that the polymer film may be applied to an individual's face or head and wherein upon dissolution of the film, the fibers remain and simulate the appearance of the individual's own hair.

More specifically, the nylon fibers ideally have the color and overall appearance of the individual's eyebrows or other surrounding hair depending upon where the fibers are applied. The fibers are magnetic responsive fibers and are oriented in a non-random direction and embedded in the matrix.

By "oriented in a non-random direction" is meant that the orientation is non-random with respect to at least one, two or three perpendicular axes. Put another way, the fibers may have some degree of orientation along one or more planes, preferably including the plane containing the dissolvable film.

The polymer film matrix is composed of one or more water-dissolvable polymers. A non-limiting list of water-dissolvable polymers contemplated by the present invention includes: water-soluble hydroxypropylmethyl cellulose (e.g., Methocel E50®, The Dow Chemical Company, Midland, Mich.), hydroxyethyl cellulose, hydroxypropyl cellulose, polyvinyl pyrrolidone, carboxymethyl cellulose, sodium carboxy methyl cellulose, methyl cellulose, polyvinyl alcohol, sodium alginate, polyethylene glycol, xanthan gum, tragacantha, guar gum, acacia gum, arabic gum, carrageenan, pullulan, chitosan, polyacrylic acid, methylmethacrylate copolymer, carboxyvinyl copolymers, and/or mixtures thereof.

The polymer film matrix may also comprise film formers which may be water soluble/dispersible or oil soluble/dispersible. Film formers may be hydrophilic or hydrophobic depending on the solvent system in the cosmetic gel. Suitable film formers include, but are not limited to, the following: one or more acrylate copolymers such as acrylate/octylacrylamide copolymers and acrylate/vinyl acetate copolymers; ethylene/acrylic acid copolymer; polyacrylic acid; $C_1$ to $C_5$ alkyl galactomannan; adipic acid/diethylene glycol/glycerin crosspolymer; trimethylpentanediol/adipic acid copolymer; trimethylpentanediol/adipic acid/isononanoic acid; polyimides; alpha olefin/isopropyl maleate/maleic anhydride polymer; acrylates $C_{10}$ to $C_{30}$ alkyl acrylate crosspolymer; polyamides; diglycol/cyclohexane-dimethanol/isophthalates/sulfoisophthalate copolymer; polyurethane resins; MQ resins such as trimethylsiloxysilicate; T resins such as polymethylsilsesquioxane; rosin resins; hydrocarbon resins; isododecane/ethylene mixed copolymer; cycloalkyl methacrylate copolymer/ isododecane; trimethyl polysiloxane octadecene/maleic anhydride copolymer; and mixtures of the foregoing. The polyurethane resins include Polyurethane-1, Polyurethane-2, Polyurethane-4, Polyurethane-5, and mixtures thereof. Additional film formers include those set forth in U.S. Pat. No. 5,916,541, which is incorporated herein by reference.

To match the fibers in the matrix with those on an individual's face to which the matrix will be applied, the fibers may be pigmented (i.e., colored) to provide a reasonably close match with the color of the individual's natural, existing hair.

Iron oxides are well known in the art to yield pigments and as such are also widely used in the cosmetic field. Iron oxides are considered to be nontoxic, moisture resistant, and non-bleeding. Iron oxides graded safe for cosmetic use are produced synthetically in order to avoid the inclusion of ferrous or ferric oxides, and impurities normally found in naturally occurring iron oxides. Typically, the iron (II) oxide pigment is black, while the iron (III) oxide is red or rust-colored. (Iron compounds other than oxides can have other colors.)

Iron (II,III) oxide is found in nature as the mineral magnetite (and is commonly known as black iron oxide) and has the chemical formula $Fe_3O_4$. It contains both $Fe^{2+}$ and $Fe^{3+}$ ions and is sometimes formulated as $FeO.Fe_2O_3$. It is encountered in the laboratory as a black powder. It exhibits permanent magnetism and is ferrimagnetic, but is sometimes incorrectly described as ferromagnetic. It's most extensive use is as a black pigment which is synthesized rather than being extracted from the naturally occurring mineral as the particle size and shape can be varied by the method of production.

In a preferred embodiment, the fibers are coated with a magnetic iron oxide. Preferred magnetic iron oxides include black iron oxide (magnetite), maghemite, carbon black, brown iron oxide, pyrrhotite, and titanium dioxide. The invention is not limited to these magnetic iron oxides and other magnetic metal oxides are contemplated by the present invention.

Iron oxide coated nylon fibers have a preferred length in the range of approximately 0.75 mm to approximately 20 mm, more preferably from approximately 0.5 mm to approximately 10 mm and most preferably from approximately 0.1 mm to approximately 5 mm, with a diameter in the range of approximately 1-30D (denier), and preferably comparable to human hair or eyelashes.

Black iron oxide fibers as described may be over coated with brown, grey, or blonde matching shades to keep the magnetic strength while providing a more versatile shade palette.

In alternative embodiments, the iron oxide coated fiber may comprise other polymers as a core, such as polyethylene (PE), polyethylene terephthalate (PET), cellulose, polypropylene (PP), acrylate, and polyurethane (PUR).

The iron coated fibers may also be provided without core and comprise hydrous iron oxides such as those described in U.S. Pat. No. 6,599,493, which is incorporated by reference fully herein.

As noted, the keratin-like fibers are magnetic responsive fibers and are advantageously nylon fibers though other fibers may be used without detracting from the invention.

Exemplary magnetic responsive nylon fibers contemplated by the embodiments disclosed herein may be obtained from KOBO Products, Inc. (South Plainfield, N.J.) and have the following trade names: NFBL-10D-2R; NFBR-10D-2R; NFBR-10D-2T, although the invention is not limited to the aforementioned fibers only. The aforementioned fibers are colored nylon fibers and commercially available in length 2 mm and a thickness of 10 Denier.

Nylon fibers obtainable from KOBO products include "Nylon Cut Fiber 6D" which includes nylon-66 plus titanium dioxide and silica is available having a length of 2 mm and a thickness of 6 Denier; "Nylon-66 Fiber 20D" which includes nylon-66 and titanium dioxide and has a fiber length of 2 mm and a thickness of 20 Denier; and "Nylon-66 Fiber 3D" which includes nylon-66 and titanium dioxide and has a fiber length of 2 mm and a thickness of 3 Denier. KOBO's KNY-1.7 fiber includes nylon-6 plus silica and titanium dioxide and has a fiber length of 1 mm and a thickness of 15 Denier.

As noted, in addition to nylon fibers, the invention further encompasses cellulose fibers, polypropylene fibers and polyethylene terephthalate fibers.

In alternative embodiments, fibers may be made from cellulose. Cellulose is a natural polymer and the fibers may be fabricated to vary in length from 20 µm to 750 µm. Cellulose fibers are hydrophilic and disperse easily in the initial water phase of an emulsion.

Cellulose Fibers obtainable from KOBO Products Inc. are sold under the tradename "Cell-U-Lash" and are available in lengths ranging from 20 µm to 750 µm.

Polypropylene fibers available from KOBO Products Inc. are sold under the tradename "PP Fiber" and incorporate silica. The propylene fibers available from KOBO Products are available in two lengths and thicknesses. PP Fiber 6D05 is provided in length 0.5 mm and 5.6 Denier thickness and PP Fiber 6D2 is available in length 2 mm and 5.6 Denier thickness.

Polyethylene Terephthalate fibers from KOBO Products Inc. are sold under the trade name "Prismatic Powder". Prismatic Powder BB35C30 is available in particle 20 µm×30 µm, while Prismatic Powder BB35C150 is available in particle size 20 µm×150 µm The invention also contemplates other pigments commonly utilized in the cosmetic art such as, but not limited to, colored pigments including organic and/or inorganic pigments, such as inorganic red pigments such as iron oxide, iron hydroxide, and iron titanate, inorganic brown pigments such as γ-iron oxide, inorganic yellow pigments such as iron oxide yellow and loess, inorganic black pigments such as iron oxide black and carbon black, inorganic violet pigments such as manganese violet and cobalt violet, inorganic green pigments such as chromium hydroxide, chromium oxide, cobalt oxide, and cobalt titanate, in organic blue pigments such as Prussian blue and In one embodiment in accordance with the present invention, a method for preparing a product for creating or enhancing the appearance of keratin fibers comprises (a) applying an external magnetic field to an aqueous mixture of one or more water-dissolvable polymers and plurality of magnetic responsive fibers so as to orient the fibers in a non-random manner; and (b) removing the aqueous solvent to form a solid or semi-solid film.

The method for preparing the product may also include additional steps of pre-coating the magnetic responsive fibers with an iron oxide as described above and additionally with other pigments to impart further coloration to the fibers.

More particularly, the method for preparing the dissolvable film matrix product for creating or enhancing the appearance of keratin fibers includes the steps of mixing one or more water dissolvable polymers with water; adding the magnetic responsive fibers to the polymer mixture; pouring the resulting mixture into a dish, preferably a flat one and applying a magnetic field to the mixture to orient the fibers in a non-random manner. The mixture is then heated at approximately 60 C for approximately 6 hours until the mixture becomes a film. After drying, the film can then be cut into desired shapes for application to an individual's eyebrows or other areas where the fibers are to be applied.

The magnetic field utilized in accordance with the present invention may be any conventional magnetic field as known in the art. For example, in the preparation of the dissolvable polymer film matrix, a magnet may be positioned in proximity to the mixture such that the magnet exerts its forces upon the magnetic responsive fibers in the dissolvable polymer film matrix. The magnetic force causes the magnetic responsive fibers to be oriented along a plane so that when the matrix is applied to an individual, the fibers simulate the appearance of the individual's natural hair.

The magnetic field, for example, may be applied using a magnetic stir plate or magnetic mixer. Magnetic stirrers often include a hot plate or some other means for heating the liquid, which may be used to facilitate removal of solvent. The invention is not limited to the use of a magnetic stir plate and the magnetic field may be applied using other methods and apparatuses know to those of skill in the art.

The magnetic field applied is measured in "Gauss". The magnetic field applied in accordance with the present invention is typically within the range of 1-250 Gauss, although the invention is not limited in this respect and stronger or weaker magnetic fields are contemplated and may be applied without detracting for the present invention.

The polymer matrix film optionally may include one or more of the following additional ingredients to modify aesthetics and/or adhesion strength: anesthetics, anti-allergenics, antifungals, antimicrobials, anti-inflammatories, antiseptics, chelating agents, colorants, depigmenting agents, emollients, fragrances, humectants, lubricants, moisturizers, pharmaceutical agents, preservatives, skin protectants, skin penetration enhancers, stabilizers, surfactants, and vitamins apart from the colored fibers to provide additional color and/or visual effects.

In addition to the pharmaceutical agents recited above, the polymer matrix film may also optionally include bioactive compounds that promote and/or restore hair growth such as, for example, Allergan's Latisse® product (bimatoprost) for treating inadequate or lack of eyelashes. Other bioactive compounds contemplated that promote and/or restore hair growth include minoxidil (Rogaine®), finasteride (Propecia®), dutasteride, ketoconazole, saw palmetto extract, various retinoids, lecithin, and the like.

Also contemplated are keratin conditioning agents. Any keratin conditioning agent known to the art as cosmetically acceptable, may be employed, for example: algae extracts (for example, BIOSTRUCTURER and BIOENERGIZER from Secma), wheat amino acids, wheat protein, hydrolyzed vegetable protein, hydrolyzed vegetable protein derivatives (for example hydrolyzed vegetable protein propylene glycol-propyl silanetriol (KERAVIS from Croda Chemicals)), keratin amino acids, serum protein, yeast extract, hydrolyzed mucopolysaccharides (for example, OLIGOQUAT M from Arch Chemicals), hydrolyzed animal protein, chitosan, phytantriol, hydrolyzed corn protein, hydrolyzed soy protein, hydrolyzed silk, silk amino acids, and mixtures thereof.

Other optional ingredients may include antioxidants, such as, rosemary extract, tocopherol, a derivative of tocopherol including a tocotriene, carotene, a carotenoid, a phenolic antioxidant including a phenolic acid, a bioflavonoid, a plant extract, curcumin, tetrahydrocurcumin, camphorol, quercetine, epigenine, and any mixtures thereof. Also, keratolytic agents, such as, salicylic acid, resorcinol, peroxide of an organic acid, and any mixtures thereof;

Filler powders are contemplated that can be physically or chemically coated with a moisturizing agent and used in the compositions of this invention. Such filler powders include, but are not limited to, mineral silicate, starch, kaolin, nylon, zinc oxide, titanium oxide, precipitated calcium carbonate, synthetic polymer powder, as well as other fillers known in the art, or any combinations thereof. The fillers may have hydrophobic or hydrophilic surfaces. The most preferred fillers are mineral silicates, such as mica and talc.

In another embodiment, the invention provides methods for applying the polymer matrix to an individual's face or head. Using the application of the matrix film to an individual's eyebrows as an example, the method provides that steps of: (a) wetting the surface of an area on an individual's face or head to which the film will be applied; (b) positioning the film on the wetted surface; and (c) allowing the film to dissolve; wherein said film includes a plurality of non-randomly oriented fibers that are adhered to said individual's face or head by a water-dissolvable polymer. As stated previously, the matrix film applied to an individual's eyebrows (for example) is typically pre-cut in a shape that complements the shape of the eyebrows upon which the film will be applied.

The matrix of water dissolvable polymers may be coated or disposed on to a backing or carrier sheet or substrate to provide structural support, to facilitate handling, storage, etc. Backing or carrier sheets are well known in the art and may include, without limitation, sheet stock, wax paper, cellophane, Teflon®, non-absorbent plastics such as lexan or polystyrene, and the like.

Optionally, the matrix may include a peelable, top or cover sheet upon the matrix film. This will protect the film during storage and transport. When the matrix film is to be applied to an individual, the top or cover sheet can be easily peeled from the matrix prior to application of the matrix to the wetted surface of the individual's face as described above.

With respect to manufacture, a slurry is typically prepared that comprises the water-dissolvable polymers and fibers. In preparing such a slurry, back injection equipment may be used to scale-up and commercialize production and manufacture. The slurry is typically pumped into a plastic form from the back into a pan which is then exposed to a magnetic field, the film would be partially dried with an absorbent paper wicking off the water and the remaining film is dried in an oven. An absorbent paper placed on top of the fiber film could serve as the substrate for the film to be laid down on the skin once the fibers are orientated. In the oven the fiber containing film could be peeled off the absorbent paper to provide a dissolvable product to deliver the fibers.

The following examples are meant to demonstrate certain aspects of the invention in a non-limiting fashion.

EXAMPLES

1. Exemplary Formulations

| | Weight Percentage | |
|---|---|---|
| Ingredients | Formula 1 | Formula 2 |
| Methocel E50 | 5 | 3 |
| Nylon fiber coated with iron oxide | 1 | 1 |
| Polyvinyl alcohol | 0 | 3 |
| Water | 94 | 93 |

2. Preparation of Dissolvable Film Polymer Matrix

One or more water-dissolvable polymers are mixed with water;

adding magnetic responsive fibers into the polymer mixture;

pouring the resulting mixture into a flat dish;

applying an external magnetic field to the mixture to orient the fibers;

heating the mixture in the flat dish at approximately 60° C. for approximately six hours until the mixture becomes a film;

cutting the film into eyebrow-like shape for application to a wearer's eyebrows (or other suitable shapes depending upon where the film will be applied).

3. Method for Applying the Eyebrow Lay Down Film Product

Wetting the surface of an area on an individual's face or head to which the dissolvable polymer film matrix will be applied;

positioning the matrix on the wetted surface; and allowing the film to dissolve;

upon dissolution of the film, the fibers incorporated in the film are adhered in place on said individual's eyebrows, beard or head.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

The invention claimed is:

1. A product for creating or enhancing the appearance of keratin fibers comprising:
   (a) a solid or semi-solid film composed of one or more water-dissolvable polymers having a plurality of magnetic responsive fibers that have been magnetically oriented, prior to application to an individual's eyebrow, in a non-random direction and embedded in said film, wherein said film is in an eyebrow-like shape; and
   (b) a backing sheet on which said film is disposed; and
   (c) a peelable cover sheet for protecting said film prior to application;
   wherein when applied to the individual's eyebrow, the plurality of magnetic responsive fibers adhere thereto in said non-random direction by said water-dissolvable polymers.

2. The product according to claim 1, where said magnetic responsive fibers comprise nylon fibers.

3. The product according to claim 2, where said nylon fibers are coated with iron oxide.

4. The product according to claim 3, where said iron oxide is magnetite.

5. The product according to claim 1, where said water-dissolvable polymer is selected from the group consisting of: water-soluble hydroxypropylmethyl cellulose, hydroxyethyl cellulose, hydroxypropyl cellulose, polyvinyl pyrrolidone, carboxymethyl cellulose, sodium carboxy methyl cellulose, methyl cellulose, polyvinyl alcohol, sodium alginate, polyethylene glycol, xanthan gum, tragacantha, guar gum, acacia gum, arabic gum, carrageenan, pullulan, chitosan, polyacrylic acid, methylmethacrylate copolymer, carboxyvinyl copolymers, and/or mixtures thereof.

6. The product according to claim 2, where said magnetic responsive fibers further include a colorant.

7. A method for preparing the product of claim 1 for creating or enhancing the appearance of keratin fibers comprising:
   (a) applying an external magnetic field to an aqueous mixture of one or more water-dissolvable polymers and plurality of magnetic responsive fibers in a flat pan so as to orient the fibers in a non-random manner;
   (b) removing the aqueous solvent by heating the composition in said flat pan to form a solid or semi-solid film having a plurality of magnetically responsive fibers oriented in a non-random direction and embedded in said film, and
   (c) cutting the film into eyebrow-like shape for application to an individual's eyebrows;
wherein when applied, the plurality of magnetic responsive fibers adhere to the individual's eyebrows in said non-random direction by said water-dissolvable polymers.

8. The method according to claim 7, where the magnetic responsive fibers are pretreated with iron oxide.

9. The method according to claim 8, wherein the iron oxide is magnetite.

10. A method for applying the keratin fiber enhancing film of claim 1 comprising:
    (a) wetting the surface of an area on an individual's eyebrows;
    (b) positioning a keratin fiber enhancing film on the wetted surface, said film comprising a plurality of magnetic responsive fibers that have been magnetically oriented, prior to application to the individual's eyebrows, in a non-random direction and a water dissolvable polymer; and
    (c) allowing the film to dissolve;
to thereby adhere the plurality of magnetic responsive fibers in said non-random direction to said individual's eyebrows by said water-dissolvable polymer.

11. The method according to claim 10, where the adhered fibers are oriented in a single direction to simulate the appearance of the individual's hair.

12. The method according to claim 10, where said fibers are magnetic responsive fibers.

13. The method according to claim 12, where said magnetic responsive fibers comprise nylon fibers.

14. The method according to claim 13, where said nylon fibers are coated with iron oxide.

15. The method according to claim 14, where said iron oxide is magnetite.

16. The method according to claim 10, where said film comprises a matrix composed of water-dissolvable polymers selected from the group consisting of: water-soluble hydroxypropylmethyl cellulose, hydroxyethyl cellulose, hydroxypropyl cellulose, polyvinyl pyrrolidone, carboxymethyl cellulose, sodium carboxy methyl cellulose, methyl cellulose, polyvinyl alcohol, sodium alginate, polyethylene glycol, xanthan gum, tragacantha, guar gum, acacia gum, arabic gum, carrageenan, pullulan, chitosan, polyacrylic acid, methylmethacrylate copolymer, carboxyvinyl copolymers, and/or mixtures thereof.

* * * * *